United States Patent [19]

Pressman et al.

[11] Patent Number: 4,584,416
[45] Date of Patent: Apr. 22, 1986

[54] METHOD AND CATALYST FOR MAKING BISPHENOL

[75] Inventors: Eric J. Pressman, Schenectady; Paul R. Willey, Scotia, both of N.Y.

[73] Assignee: General Electric Company, Schenectady, N.Y.

[21] Appl. No.: 551,624

[22] Filed: Nov. 14, 1983

[51] Int. Cl.⁴ .............................................. C07C 39/16
[52] U.S. Cl. .................................... 568/727; 568/728; 521/32
[58] Field of Search .......................................... 521/32

[56] References Cited

U.S. PATENT DOCUMENTS

| 3,394,089 | 7/1968 | McNutt et al. | |
| 4,346,247 | 8/1982 | Faler | |
| 4,396,728 | 8/1983 | Faler | |
| 4,424,283 | 1/1984 | Faler | |
| 4,478,956 | 10/1984 | Maki et al. | 54/32 |

Primary Examiner—Joseph L. Schofer
Assistant Examiner—Peter F. Kulkosky
Attorney, Agent, or Firm—William A. Teoli; James C. Davis, Jr.; James Magee, Jr.

[57] ABSTRACT

A sulfonated aromatic organic polymer, such as sulfonated polystyrene ion-exchange resin is provided having ionically bound N-alkylaminoorganomercaptan groups. The ion-exchange resin can be used to effect phenol-ketone condensation.

9 Claims, No Drawings

METHOD AND CATALYST FOR MAKING BISPHENOL

CROSS REFEREMCE TO RELATED APPLICATIONS

Reference is made to copending application of Gary R. Faler and R. George Loucks Ser. No. 342,435, filed Jan. 25, 1982, now U.S. Pat. No. 4,424,283, for Catalyst for Synthesizing Bisphenol and Method for Making Same.

BACKGROUND OF THE INVENTION

Prior to the present invention, various methods were employed to synthesize bisphenols, such as bisphenol-A, by effecting reaction between a ketone and a phenol. One procedure, for example, involved the use of large amounts of inorganic acid catalysts, such as sulfuric acid or hydrochloric acid. Experience has shown, however, that the use of inorganic acids requires a means to neutralize such acids at the end of the reaction due to the corrosive action of the strong acids. In addition, distillation of the resulting bisphenol is often required because of the many by-products formed during the reaction under high acid conditions.

An improved procedure was developed to synthesize bisphenols by using a solid resin cation-exchange catalyst to effect phenol-ketone condensation. A disadvantage of the ion-exchange catalyst, however, is its relatively low acid concentration resulting in slow reaction rates. Rate acceleration has been achieved through the use of mercaptans. Apel et al. U.S. Pat. No. 3,153,001, shows incorporation of mercaptan by partial esterification of the ion-exchange catalyst in the form of a sulfonated insoluble polystyrene resin. Another procedure (McNutt et al, U.S. Pat. No. 3,394,089) shows the partial neutralization of aromatic sulfonic acid with alkylmercaptoamine. A further procedure is shown by Wagner et al. U.S. Pat. No. 3,172,916, based on the partial reduction of the sulfonic acid to afford thiophenol functional groups.

Further improvements in synthesizing bisphenols from ion-exchange resins are shown by Faler et al. U.S. Pat. Nos. 4,294,995, 4,346,247, and 4,396,728, assigned to the same assignee as the present invention and incorporated herein by reference. Faler et al. utilize certain N-organoaminodisulfide to incorporate covalently bonded organomercaptan groups into the backbone of sulfonated aromatic organic polymer.

Although particular improvements have been obtained by using ion-exchange resins of the prior art, it has been found that available ion-exchange resins comprising sulfonated aromatic organic polymer having chemically combined aminoorganomercaptan groups do not provide a satisfactory degree of activity, selectivity and stability with respect to catalyzing the conversion of a ketone to a bisphenol as a result of reaction with a phenol.

As utilized hereinafter, the expression "catalyst activity", or "% conversion" (% C) means $$\frac{\text{pbw ketone converted(bisphenol)}}{\text{pbw ketone used}} \times 100 = \% C$$

Catalyst activity is calculated under continuous steady-state reaction conditions from data obtained at a temperature of 60° C. to 85° C. In measuring catalyst activity, ion-exchange resin is used having an attachment level of about 4 to 40 mole percent of aminoorganomercaptan sites, at a Weight—Hour—Space—Velocity (WHSV) averaging about 3.0 to 16.0 parts of feed, per part of ion-exchange resin, per hour.

The expression "selectivity", or "S", is specific to the production of bisphenol-A and is calculated as follows:

$$\frac{\text{pbw of p-p-bisphenol-A}}{\text{pbw of o-p-bisphenol-A}} = S$$

The selectivity value is also calculated from data obtained under continuous steady state and WHSV conditions as defined above.

The term "stability" with respect to defining the characteristics of ion-exchange resins having chemically combined aminoorganomercaptan groups means the ability to resist change in % conversion and selectivity under continuous steady-state operating conditions as previously defined. In calculating ion-exchange resin stability, an initial average "base" value for % conversion and selectivity is determined over a period of up to 4 days under continuous steady-state conditions. A subsequent average "trial" value for % conversion and selectivity is thereafter computed by continuous use of the ion-exchange resin for a period of up to 60 days. Catalyst stability is expressed as follows as a % conversion variance "% CV" over the trial period:

$$\% CV = \frac{\text{Base \% Conversion} - \text{Trial \% Conversion}}{\text{Base \% Conversion}} \times \frac{100}{1}$$

The present invention is based on the discovery that substantial improvements in conversion of acetone to bisphenol, and higher yields of p-p-bisphenol-A can be obtained by using effective amounts of sulfonated aromatic organic polymer having from about 4 to 40 mole percent of ionically bound aminoorganomercaptan groups of the formula,

where R is a $C_{(3-10)}$ divalent organo radical, and $R^1$ is a $C_{(3-8)}$ monovalent alkyl radical.

For example, it was found that sulfonated cross-linked polystyrene resin having about 24 mole percent of ionically bound n-propylaminopropylmercaptan groups within the scope of formula (1) provided a 69% conversion of acetone and had a selectivity of 45.8 during an initial 4 days continuous run which fell to only a 68.8% conversion and a selectivity of 44.8 after 25 to 28 days of continuous operation. This was found to be substantially superior to sulfonated cross-linked polystyrene resin having about 21 mole percent of ionically bound aminoethylmercaptan groups which showed under the same continuous reaction conditions for making bisphenol-A, a 57.0% conversion and a selectivity of only 27 which was substantially maintained over a 25–28 day period. On the other hand, a sulfonated cross-linked polystyrene resin having about 18 mole percent of covalently bound propylaminopropylmercaptan groups, had a % conversion of 71.9 and a selectivity of 35.2 after the four day base period which fell to a % conversion of less than 40 and a selectivity of less than 24 after a 25–28 day trial run.

STATEMENT OF THE INVENTION

There is provided by the present invention an ion-exchange resin comprising sulfonated aromatic organic polymer having ionically bound N-alkylaminoorganomercaptan groups of formula (1).

There is also provided by the present invention a method for making bisphenol which comprises reacting a ketone and a phenol in the presence of an effective amount of a cation-exchange resin comprising a sulfonated aromatic organic polymer having from about 4 to 40 mole percent and preferably 25 to 35 mole percent of chemically combined sulfonated aromatic organic units with ionically bound N-alkylaminoorganomercapto radicals of formula (1).

There are included by the $C_{(3-10)}$ diorgano radicals of R of formula (1) alkylene radicals for example, trimethylene, tetramethylene, pentamethylene, hexamethylene, etc.; aromatic radicals, for example, phenylene, xylylene, tolylene, naphthylene, etc. R also includes substituted alkylene and arylene radicals as previously defined, for example, halo substituted for example, chloro, bromo, fluoro, etc. There are included by $R^1$ radicals of formula (1) monovalent alkyl radicals such as propyl, butyl, pentyl, hexyl, heptyl, and octyl.

The sulfonated aromatic organic polymer which can be used in the practice of the present invention to make ion-exchange catalyst having ionically bound alkylaminoorganomercaptan groups of formula (1) include, for example, Amberlite-118, manufactured by the Rohm and Haas Company, Dowex 50WX4, manufactured by Dow Chemical Company and other sulfonated aromatic organic polymers such as sulfonated polystyrenes which have been crosslinked with divinylbenzene.

Phenols which can be used in the practice of the present invention to make bisphenol include, for example, phenol and substituted phenols, such as

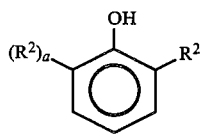

where $R^2$ is a monovalent $C_{(1-8)}$ alkyl radical, for example, methyl, ethyl, propyl, etc., and a is equal to 0 or 1.

Ketones which can be employed in the practice of the present invention to make bisphenols are, for example, acetone, diethylketone, methylethylketone, cyclohexanone, acetophenone, etc.

The ion-exchange resins of the present invention can be prepared by effecting reaction between sulfonated aromatic organic polymer and N-alkylaminoorganomercaptan monomer which can be in the form of the hydrohalide or corresponding hydrotosylate. A convenient synthesis of the N-alkylaminoorganomercaptan hydrotosylate, for example, can involve an initial reaction between a bromochloroalkane and an alkali metal thiosulfate which can be refluxed in an inert atmosphere in an organic solvent such as aqueous methanol. There can be added to the resulting reaction mixture an appropriate alkyl amine which can be further refluxed. Methanol and excess alkyl amine can be distilled from the mixture and isopropanol added to remove the water by azeotropic distillation. The alkylaminoorganothiosulfate and by-product alkali metal halide can then be isolated free of water by filtration of the isopropanol slurry.

A mixture of the above alkylaminoorganothiosulfate and paratoluenesulfonic acid monohydrate with methanol can be refluxed under nitrogen, followed by a standard organic extraction and work up which provides the desired product in a chlorinated hydrocarbon solvent. The tosylate salt can then be precipitated by addition of an appropriate aliphatic hydrocarbon solvent and isolated by filtration.

The ion-exchange resin catalyst of the present invention having ionically bound N-alkylaminoorganomercaptan groups can be made by effecting reaction between the sulfonated aromatic organic polymer and the N-alkylaminoorganomercaptan salt in the form of a halide salt or tosylate salt as described above. The sulfonated aromatic organic polymer in the form of a dry resin can be initially analyzed for sulfonic acid content by a standard neutralization technique and typically contains 22.1 millimoles of sulfonic acid groups per 4.70 grams of dry resin. An appropriate amount of the hydrohalide or hydrotosylate salt of the aminoorganomercaptan (typically 0.25 equivalents relative to sulfonic acid groups on the base resin) is heated as an aqueous solution in the presence of the base resin. The mixture can be heated at a temperature in the range of from 60° C. to 70° C. for 4 hours while being slowly agitated and thereafter allowed to cool to room temperature. The resulting ion-exchange catalyst can thereafter be filtered, washed with water, methanol and then vacuum oven dried.

The percent nitrogen in the ion-exchange catalyst can be determined by the Kjeldahl method (Z. Anal. Chem. 22, (1883)). From this data, nitrogen milliequivalency/gram of dry catalyst can be determined which shows the fraction of total sulfonic acid sites occupied by N-alkylaminoorganomercaptan groups of formula (1). Mercaptan milliequivalency/per gram of dry catalyst can be determined using Ellman's reagent (A. Fontana and C. Toniolo, The Chemistry of the Thiol Group, S. Patai, Editor, John Wiley and Sons, Ltd., London (1979), pp. 288–290).

With respect to the preparation of bisphenols utilizing sulfonated aromatic organic polymer containing N-alkylaminoorganomercaptan groups of the present invention, a mixture of phenol and ketone can be heated in the presence of the cation-exchange resin prepared in accordance with the practice of the present invention. There can be utilized 2–20 moles of the phenol per mole of the ketone which can be heated at a temperature in the range of from 50° C. to 110° C. with agitation. The ion-exchange resin can be employed at from 0.1% to 10% by weight, based on the weight of the total mixture in instances where a batch process is used. In a preferred procedure for making bisphenol in a continuous manner, the ion-exchange resin can be used in a column which can be operated at a temperature of 50° C. to 100° C. The mole ratio of reactants can vary widely, such as from about 3 to 1 to about 20 to 1 moles of phenol per mol of ketone. It is preferred, however, to use the reactants at a mole ratio of about 4 to 1 to about 12 to 1 moles of phenol per mol of ketone.

One method of recovering the bisphenol reaction product, for example, Bisphenol-A, is by crystallizing the BPA/phenol adduct from the reactor effluent and recovery of the bisphenol-A by distillation or crystallization. Other procedures are, for example, distillation of the reaction mixture to separate the phenol and bisphenol, or by partial distillation to remove the phenol followed by recrystallization of the residual bisphenol using water, methanol, acetonitrile, methylene chloride or toluene as the solvent. A crystallization procedure for BPA recovery is also shown by G. R. Faler, U.S. Pat. No. 4,375,567, assigned to the same assignee as the present invention and incorporated herein by reference.

In order that those skilled in the art will be better able to practice the invention, the following example is given by way of illustration and not by way of limitation. All parts are by weight.

EXAMPLE 1

A mixture of 50 grams of bromochloropropane, 78.8 grams of sodium thiosulfate pentahydrate, 250 ml of methanol and 50 ml of water was heated at reflux with stirring under a nitrogen atmosphere for 1.75 hours. The solution was allowed to cool to 35° C. and 110 ml of n-propylamine was added to the mixture. The mixture was then refluxed for 16 hours. The mixture was then distilled until 190 ml of distillate was collected. There was added 1250 ml of isopropanol to the mixture and the distillation was continued. A total of 1170 ml distillate was collected. The mixture was allowed to cool to 60° C. with stirring and 100 ml of n-heptane was added. The mixture was cooled to room temperature, filtered and washed with three portions of n-heptane and vacuum oven dried. Based on method of preparation, there was obtained 113 grams of a free flowing white powder in the form of N-propylaminopropanethiosulfate.

A mixture of 113.05 grams of the above N-propylaminopropanethiosulfate, 60.45 grams of paratoluenesulfonic acid monohydrate and 650 ml reagent grade methanol was heated at reflux with stirring under a nitrogen atmosphere. The mixture was refluxed for one hour and then cooled to room temperature. The resulting slightly cloudy yellow solution was then treated with 150 ml of water containing 20 grams of para-toluenesulfonic acid monohydrate and 400 ml of chloroform. The aqueous phase was recovered and washed with a 200 ml portion of chloroform followed by three 100 ml portions of chloroform. The organic layers were extracted with 150 ml water and then concentrated to 150 ml and allowed to cool to room temperature. There was then added 300 ml of n-heptane over a 10 minute period with stirring to provide a white yellow slurry. After stirring an additional 10 minutes, the slurry was filtered, washed with n-heptane several times and vacuum oven dried for three hours at 55° C. to provided 43.4 grams of a free flowing white powder. Based on method of preparation, the product was 3-propylamino-1-propylmercaptan hydrotosylate.

Five grams of Amberlite-118 was washed with 60 ml of water and 2×60 ml of methanol. The resulting resin was then dried for 12 hours in a vacuum oven at 55° C. to provide 4.7 grams of a sulfonated polystyrene having 22 millimoles of sulfonic acid groups. A mixture of 4.7 grams of the resin, 24 ml of water and 1.680 grams of the above 3-propylamino-1-propylmercaptan hydrotosylate was heated at 60°-70° C. for 4 hours. The resin was then washed with water and methanol and air dried for several minutes and then dried in a vacuum oven at 50° C. for 1 hour. There was obtained 5.6 grams of sulfonated polystyrene having about 24 mole percent of ionically bound 3-propylamino-1-propylmercaptan groups based on nitrogen analysis and the use of Ellman's reagent to determine mercaptan attachment level.

A feed mixture having an 8:1 mole ratio of phenol-acetone was pumped into a column containing the active catalyst at a WHSV of 4. The column was maintained at a temperature of 70° C. The effluent was sampled daily and analyzed over a period of 28 days using HPLC to determine % conversion, selectivity and catalyst stability.

In accordance with the above procedure, the same sulfonated polystyrene was used to prepare ion-exchange catalyst in accordance with the procedure of Faler U.S. Pat. No. 4,396,728 having about the same attachment level of covalently bonded 3-propylamino-1-propylmercaptan groups. Another ion-exchange resin was prepared having about the same attachment level, except that aminoethylmercaptan hydrochloride was substituted for the 3-propylamino-1-propylmercaptan hydrotosylate. The % conversion, selectivity and stability of the catalysts were then determined over a 28 day period under continuous operation as shown by the following results, where "Invention" means ion-exchange resin having ionically bound 3-propylamino-1-propylmercaptan groups, "Covalent" means the resin prepared in accordance with Faler U.S. Pat. No. 4,396,728, "Ionic Aminoethylmercaptan" means the ion-exchange resin outside the scope of formula (1), % C means % conversion and % S means % selectivity:

TABLE I

| Catalyst | Day 1-4 % C | S | Days 25-28 % C | S |
|---|---|---|---|---|
| Invention | 69.0 | 45.8 | 68.8 | 44.4 |
| Covalent | 71.9 | 35.2 | <40 | <24 |
| Ionic Aminoethylmercaptan | 57.0 | 27.0 | 56.2 | 26.0 |

The above results show that the ion-exchange catalyst of the present invention having ionically bound 3-propylamino-1-propylmercaptan groups is superior as an ion-exchange catalyst with respect to % conversion, selectivity and stability when compared to prior art ion-exchange resins.

EXAMPLE 2

A mixture of 4.70 grams of Amberlite-118 containing 22.1 millimoles of sulfonic acid groups which had been washed with water and methanol and vacuum dried at 55° C. for 12 hours was heated in 25 ml of water with 0.25 equivalents (relative to the sulfonic acid groups on the base resin) of the appropriate aminoalkylmercaptan hydrochloride or hydrotosylate salt. The mixture was heated at 60°-70° C. for 4 hours while being slowly stirred and then allowed to cool to room temperature. The resulting ion-exchange catalyst in the form of a sulfonated polystyrene resin having ionically bound aminoalkylmercaptan groups was then recovered by filtering the mixture and washing the residue with three 60 ml portions of water, three 60 ml portions of methanol and vacuum oven drying the washed product at 50° C. at 5 torr for about 12 hours. The following table shows the catalyst prepared:

TABLE II

Ionically Bound Aminoalkylmercaptan Catalyst $$\left(\begin{array}{c}-CH-CH_2-\\ \bigcirc \\ | \\ SO_3^{\ominus}R^3H_2\overset{\oplus}{N}(CH_2)_2SH\end{array}\right)_x \left(\begin{array}{c}-CH-CH_2-\\ \bigcirc \\ | \\ SO_3H\end{array}\right)_y$$

| Catalyst | $R^3$ | n | x | y |
|---|---|---|---|---|
| 1 | H | 2 | 0.21 | 0.79 |
| 2 | $C_3H_7$ | 3 | 0.24 | 0.76 |
| 3 | $C_3H_7$ | 2 | 0.24 | 0.76 |
| 4 | H | 3 | 0.21 | 0.79 |
| 5 | $C_3H_7$ | 4 | 0.21 | 0.79 |
| 6 | H | 4 | 0.21 | 0.75 |
| 7 | H | 5 | 0.25 | 0.75 |
| 8 | H | 6 | 0.23 | 0.77 |

The ion-change catalysts shown in Table II were then evaluated for catalyst activity by pumping an 8:1 phenol:acetone mole ratio solution at a WHSV of 4 through a column containing the catalyst at 70° C. The effluent was sampled daily and analyzed by HPLC over 2 days. The following table shows catalyst effectiveness in terms of % conversion and selectivity:

TABLE III

| Catalyst | % Conversion | Selectivity |
|---|---|---|
| 1 | 57 | 27 |
| 2 | 69 | 46 |
| 3 | 59 | 31 |
| 4 | 72 | 48 |
| 5 | 67 | 42 |
| 6 | 72 | 53 |
| 7 | 54 | 58 |
| 8 | 67 | 55 |

Evaluation of the ion-exchange catalysts shown in Table II was then continued following the same procedure illustrated in Table III by continuing the phenolacetone reaction for a period of up to 12 days to determine whether any change in catalyst stability was effected. The following results were obtained:

TABLE IV

| Catalyst | 1-2 Days<br>% Conv. (Selectivity) | 9-12 Days<br>% Conv. (Selectivity) |
|---|---|---|
| 1 | 57 (27) | 56 (26) |
| 2 | 69 (46) | 70 (43) |
| 3 | 59 (31) | 56 (31) |
| 4 | 72 (48) | 48 (46) |
| 5 | 67 (42) | 61 (41) |
| 6 | 72 (53) | 60 (47) |
| 7 | 54 (58) | 32 (46) |
| 8 | 67 (55) | 50 (47) |

The results shown in Tables III and IV establish that the ion-exchange catalyst having ionically bound alkylaminoalkylmercaptan groups within the scope of formula (1), as shown by catalysts 2 and 5, are superior to the other ion-exchange catalysts having ionically bound alkylaminoalkylmercaptan groups outside the scope of formula (1), if the total results shown for % conversion, selectivity and stability are considered together. Extended stability studies further established that catalysts 1 and 2 showed the smallest variance in stability over a 56 day period even though catalyst 2 within the scope of the invention exhibited superior % conversion and selectivity. It is not completely understood why a loss of stability was shown in catalysts 4 and 6-8, where n of Table II showed a value of at least 3 carbon atoms between the nitrogen atom and the sulfur atom. One possible explanation as shown by the performance of catalysts 2, 3 and 5 is that a side chain within the scope of formula (1) stabilizes the catalyst.

EXAMPLE 3

4-propylamino-1-butylmercaptan hydrochloride was prepared by the following procedure:

There was added 1.8 ml of propylamine to a stirred solution of 1.985 grams of thiobutyrolactone in 10 ml of tetrahydrofuran. The addition took place over a 5 minute period at room temperature. The resulting solution was stirred at room temperature for 2 hours, followed by heating for 1 hour, cooling to room temperature and further stirring for 12 hours. Volatiles were removed from the mixture under reduced pressure to provide 3.12 grams of the desired mercaptoamide as a colorless oil.

There was added 2.97 grams of iodine portion wise to a mixture which was stirring under nitrogen and cooled in an ice water bath consisting of 3.12 grams of the above mercaptoamide and 15 ml of ethanol. The resulting red solution was stirred for 10 minutes and then 2.48 grams of sodium carbonate was added. There was then added to the mixture after 1 hour at 0° C., 2.5 grams of sodium bisulfite. There was then added 3 grams of sodium thiosulfate to the mixture. The mixture was partitioned between water and chloroform. The aqueous layer was washed with chloroform and the combined organic layers dried over anhydrous potassium carbonate, filtered and concentrated. There was obtained 2.71 grams of a white solid. Based on method of preparation, the white solid was the corresponding bisamide disulfide.

There was added 959 milligrams of the above bisimide disulfide dissolved in 15 ml tetrahydrofuran over a period of 1 minute to a mixture of 378 milligrams of lithium aluminum hydride and 10 ml of tetrahydrofuran which was stirring under a nitrogen atmosphere. The mixture was stirred at room temperature for 45 minutes and then refluxed for 15 hours. Upon cooling to room temperature the reaction mixture was quenched by adding 0.4 ml water, 0.4 ml 15% aqueous NaOH and 1.2 ml of water and stirred at room temperature for 3 hours. The mixture was filtered through Celite and the cake washed with 100 ml portions of chloroform and water. The aqueous layer was treated with sodium bicarbonate until slightly basic and extracted twice with 50 ml portions of chloroform. The combined chloroform solutions were concentrated to 15 ml and treated with gaseous HCl at 0° C. for 15 minutes. Upon concentrating the solution, there was obtained 609 mg of a white solid or a 47% yield. The white solid was 4-propylamino-1-butylmercaptan hydrochloride based on NMR spectra and Ellman's analysis.

Although the above examples are directed to only a few of the very many variables which can be used to make the sulfonated aromatic organic polymer ion-exchange resin of the present invention having N-alkylaminoorganomercaptan groups attached to backbone sulfonyl radicals by ionic ammonium-sulfonate linkages as well as the use of such ion-exchange resin as a catalyst for making bisphenols, it should be understood that a much broader variety of N-alkylaminoorganomercaptans as well as sulfonated aromatic organic polymer can be used to make such ion-exchange resin as well as phenols and ketones which can be used to make bisphenols as shown by the description preceding these examples.

What we claim as new and desire to secure by Letters Patent of the United States is:

1. An ion-exchange resin comprising sulfonated aromatic organic polymer having 4 to 40 percent of ionically bound aminoorganomercaptan groups of the formula

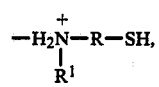

based on the total moles of chemically combined sulfonated aromatic organic units and sulfonated aromatic organic units having ionically bound aminoorganomercaptan groups where R is a $C_{(3-10)}$ divalent organo radical, and $R^1$ is a $C_{(3-8)}$ monovalent alkyl radical.

2. An ion-exchange resin in accordance with claim 1, where R is trimethylene.

3. An ion-exchange resin in accordance with claim 1, where $R^1$ is propyl.

4. An ion-exchange resin in accordance with claim 1, wherein R is trimethylene and $R^1$ is propyl.

5. An ion-exchange resin in accordance with claim 1, where the sulfonated aromatic organic polymer is sulfonated polystyrene.

6. An ion-exchange resin in accordance with claim 1, where R is tetramethylene and $R^1$ is propyl.

7. A method for making bisphenol which comprises reacting a ketone and a phenol in the presence of an effective amount of a cation-exchange resin comprising a sulfonated aromatic organic polymer having from about 4 to 40 mole percent of chemically combined sulfonated aromatic organic units with ionically bound N-alkylaminoorganomercapto radicals of the formula

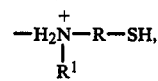

based on the total moles of chemically combined sulfonated aromatic organic units and sulfonated aromtic organic units having ionically bound aminoorganomercaptan groups where R is a $C_{(3-10)}$ divalent organo radical, and $R^1$ is a $C_{(3-8)}$ monovalent alkyl radical.

8. A method for making bisphenol in accordance with claim 7 utilizing acetone and phenol.

9. A method for making bisphenol in accordance with claim 7 utilizing ion-exchange resin having 25-35 mole percent of ionically bound propylaminopropylmercaptan groups.

* * * * *